United States Patent
Matsumoto et al.

(10) Patent No.: US 6,946,573 B2
(45) Date of Patent: Sep. 20, 2005

(54) METHOD FOR STARTING UP REACTOR AND REACTOR SYSTEM

(75) Inventors: Yukihiro Matsumoto, Kobe (JP); Takeshi Nishimura, Himeji (JP); Hideki Sogabe, Kobe (JP); Kazuhiko Sakamoto, Himeji (JP); Osamu Dodo, Hyogo (JP)

(73) Assignee: Nippon Shokaubai Co., Ltd., Osaka (JP)

( * ) Notice: Subject to any disclaimer, the term of this patent is extended or adjusted under 35 U.S.C. 154(b) by 798 days.

(21) Appl. No.: 09/845,694

(22) Filed: Apr. 30, 2001

(65) Prior Publication Data

US 2001/0024630 A1 Sep. 27, 2001

(30) Foreign Application Priority Data

May 2, 2000 (JP) .......................................... 2000-133577

(51) Int. Cl.$^7$ .............................................. C07C 57/02
(52) U.S. Cl. ...................................................... 562/598
(58) Field of Search ......................................... 562/598

(56) References Cited

U.S. PATENT DOCUMENTS

| | | | |
|---|---|---|---|
| 3,634,502 A | * | 1/1972 | Eden ........................... 562/545 |
| 3,762,465 A | | 10/1973 | Gutlhuber |
| 6,046,343 A | | 4/2000 | Mummey et al. ........... 549/259 |

FOREIGN PATENT DOCUMENTS

GB  1 089 353  1/1967

* cited by examiner

Primary Examiner—Paul A. Zucker
(74) Attorney, Agent, or Firm—Mathews Shephard McKay & Bruneau, P.A.

(57) ABSTRACT

A method for quickly starting up a reactor and a reactor system therefor are provided. A shell-and-tube reactor in the system is adapted to circulate a heat medium having a solid point in the range of 50–250° C. to the outside of the reaction tubes and characterized by initiating temperature elevation of the reactor by introducing a gas of a temperature in the range of 100–400° C. to the reaction tubes' side and then circulating the heat medium in a heated state to the outside of the reaction tubes. By introducing a gas of an elevated temperature preparatorily to the reaction tubes, it is made possible to prevent the heat medium after circulation from being solidified again and enable the reactor to be quickly started up.

9 Claims, 3 Drawing Sheets

METHOD FOR STARTING UP REACTOR AND REACTOR SYSTEM

BACKGROUND OF THE INVENTION

1. Field of the Invention

This invention relates to a method for starting up a reactor and a reactor system. More particularly, this invention relates to a method for starting up a reactor and a reactor system in producing (meth)acrylic acid and/or (meth) acrolein by the reaction of catalytic gas phase oxidation.

2. Description of Related Art

Acrylic acid is used as coating materials, fiber processing materials, leather processing materials, and building materials in addition to being adopted as a copolymer for acrylic fibers or in the form of emulsion for an adhesive agent. It has been filling a growing demand from the applications concerned. Thus, the desirability of developing a process which produces the acrylic acid from less expensive raw materials, allows expansion of the plant operated for the production, and entails environmental pollution only sparingly has been finding enthusiastic approval. The acrylic acid is generally produced by the reaction of catalytic gas phase oxidation of propylene, for example.

This reaction of catalytic gas phase oxidation for the production of acrylic acid, for example, is exothermal in nature. The maintenance of this exothermal reaction at a constant temperature is generally accomplished by circulating a heat medium with a pump to cool the reaction tube and then cooling the heat medium with a cooling device connected to the path of circulation.

At the time of starting up the reaction of catalytic gas phase oxidation in such a reactor, however, the reactor must be preheated, in advance of the supply of a raw material gas, in order to rise a temperature for promoting the reaction. Thus, a reactor of the so-called shell-and-tube type which is furnished as a heating means operated exclusively during the time of starting up with a heating device disposed additionally outside the reactor, connected to the reactor in the vicinity of the terminal part of the bundle of reaction tubes, and allowed to have a composite closing-adjusting mechanism installed at the site of connection has been disclosed in the official gazette of U.S. Pat. No. 3,762,465.

The heat medium which is used in the reactor of this sort is known in such types as organic heat medium, fused salt, and fused metal. Though the organic heat medium is widely used, it allows no safe use from the viewpoint of thermal stability at elevated temperatures exceeding 350° C. Generally, therefore, the fused salt (commonly called "niter") is often used as a heat medium to be used at temperatures in the range of 350–550° C.

The composition of this niter embraces a mixture comprising 43% of sodium nitrite, 7% of sodium nitrate and 53% of potassium nitrate and a mixture consisting of 50% of sodium nitrite and 50% of potassium nitrate, for example. The solid point of the former mixture is 142° C., it is known that the niter has the solid point thereof rise when the mixing ratio of the components thereof varies and that the niter while in service suffers the solid point thereof to rise when the nitrous acid is converted into sodium nitrate by decomposition or oxidation. Generally, the reactor which uses the niter of this nature as a heat medium, therefore, is more often than not designed on the assumption that the solid point of this heat medium is 180° C.

When propylene, for example, is oxidized by using a catalyst for contact gas phase oxidation, the niter which is in a solid state at atmospheric temperature can maintain a fused state and attain easy circulation inside the reactor because the reaction temperature is higher than the solid point of the heat medium and the reaction itself is exothermal in nature. Since the reactor at the time of starting up is at a temperature lower than the solid point of the heat medium, however, the temperature of the reactor must be elevated till the heat medium in the reactor assumes a fused state.

FIG. 2 is a type section illustrating a large reaction apparatus for the production of phthalic anhydride, maleic anhydride, acrylic acid, and methacrylic acid, for example, and a route for the circulation of a heat medium therein. The flow of the heat medium at the time of starting up this reaction apparatus for the production of acrylic acid may be described as follows. With reference to FIG. 2, 101 stands for a reactor, 102 for an axial pump, 103 for a steam generator, 103' for a boiler feed water, 103" for steam, 104 and 106 each for a heater, 105 for a heat medium tank, and 107 for a pump. When the niter is used as the heat medium, since the niter is in a solid state at atmospheric temperature, the practice of discharging the niter from the reactor and putting it to storage in a heat medium tank after the use of the reactor is completed prevailing. The method for starting up the reactor in this case will be described.

First, the heat medium stored in the heat medium tank 105 is heated with the heater 104 passing steam therethrough till it is fused. The heat medium is supplied with the pump 107 to the reactor 101, circulated with the axial pump 102 to the fluid outside the tubes in the reactor, and thereafter heated with the electric heater 106 for elevation of the temperature thereof. The steam generator 103 is used for cooling the heat medium heated to an unduly high temperature or removing the heat of reaction after introduction of the raw material gas.

When the niter is used as the heat medium during the time of starting up the reactor, the reactor 101 itself may be heated for elevation of temperature with the electric heater 106 as illustrated in FIG. 2 or the heat medium heated with the electric heater for temperature elevation may be supplied to the reactor 101 as described above.

When the heat medium is circulated by the use of the heating device disposed simply outside the reactor as described in the official gazette of U.S. Pat. No. 3,762,465, the inside of the reaction tube is not heated till a fully satisfactory elevated temperature. Particularly during the time of starting up the reaction of catalytic gas phase oxidation, therefore, the circulation of the heat medium requires a long time and the shift of the reaction to the normal condition necessitates an unduly long time.

Further, since the heat medium has the density thereof vary with temperature, the total volume thereof is varied in accordance as the rate of reaction and the amount of the heat of reaction to be generated proportionately therewith are changed. Absolutely no measure, however, has been heretofore adopted for moderating the change of the volume proportionate with the change in the density of the heat medium. Rather the use of an apparatus capable of resisting pressure has been barely resorted to.

Particularly, when the compound at which the production is aimed happens to be acrylic acid, there are times when the reaction is performed in two stages, one for obtaining acrolein from propylene as the raw material and the other for subsequently obtaining acrylic acid from the acrolein. In this case, besides the procedure which comprises using a first reactor in the first reaction for the production of acrolein from propylene and a second reactor in the second reaction for the production of acrylic acid from acrolein, the procedure which, by the use of a reactor partitioned with an intermediate tube sheet into a first chamber and a second chamber, effects the first reaction in the first chamber and the second reaction in the second chamber may be adopted. In any event, in the process of production which combines a plurality of modes of reaction, as many reactors as the modes of reaction must severally attach heat medium heating devices and this annexation proves uneconomical from the viewpoint of equipment design and tends to complicate the work environment. In contrast, when the exothermal reaction is performed in the normal condition, since the heat medium is cooled outside the reactor and put to cyclic use, the heating devices which are not used unless at the time of starting up form an excess of equipment.

SUMMARY OF THE INVENTION

The present inventor, after pursuing a diligent study in search of a method for starting up a reactor to be used in the reaction of catalytic gas phase oxidation, has found that when a gas heated in advance to an elevated temperature is supplied from the reaction tube side and, at the same time, a heat medium heated in advance is supplied to the reactor, the reactor is very efficiently enabled to assume temperature conditions optimum for the reaction of catalytic gas phase oxidation and that when the reactor system used for the reaction has a specific means for storing a heat medium and a heating means specifically laid out therein, the reactor is enabled to be very efficiently heated with one heating device to an elevated temperature. This invention has been perfected as a result. To be specific, the task imposed on this invention is accomplished by the following items.

(1) In a shell-and-tube type reactor adapted to circulate a heat medium having a solid point in the range of 50–250° C. to the outside of the reaction tubes, a method for starting up the reactor characterized by introducing a gas of a temperature in the range of 100–400° C. into the reaction tubes thereby initiating temperature elevation and then circulating the heat medium in a heated state to the outside of the reaction tubes.

(2) A method for the production of (meth)acrylic acid and/or (meth)acrolein, characterized by supplying a raw material gas to the reactor after the method for starting up the device set forth in (1) above.

(3) A reactor system comprising a reactor forming therein a plurality of chambers partitioned with an intermediate tube sheet, means for storing a heat medium led out of said chambers, heating means for heating the heat medium led out of said storing means, and means for supplying said heat medium heated by said heating means to an elevated temperature to at least one of said chambers, characterized by the fact that said storing mean comprises one tank capable of storing at least part of the heat medium in said component chambers and said tank has a volume smaller than the amount of the heat medium circulated within the component chambers.

(4) A reactor system comprising a reactor, means for storing a heat medium led out of said chambers, heating means for heating the heat medium led out of said storing means, and means for supplying said heat medium heated by said heating means to an elevated temperature to at least one of said chambers, characterized by the fact that said storing mean comprises one tank capable of storing at least part of the heat medium in said component chambers, said tank has a volume smaller than the amount of the heat medium circulated within the component chambers, and a pile for introducing the heat medium into the reactor is connected to the reactor from an upper annular conduit of said reactor or from the part at a level higher than said annular conduit.

According to this invention, it is made possible to curtail the time for heating the reactor to an elevated temperature and shorten the time for starting up. Particularly, the method for starting up the reactor contemplated by this invention enables the heat medium circulated to a reactor possessing different temperature ranges as in the reaction of two-stage catalytic gas phase oxidation of (meth)acrylic acid, for example, to be heated efficiently to an elevated temperature by simply having one electric heater connected to the reactor and consequently curtailing the time for starting up the reactor.

DESCRIPTION OF THE PREFERRED EMBODIMENTS

Figure 1:
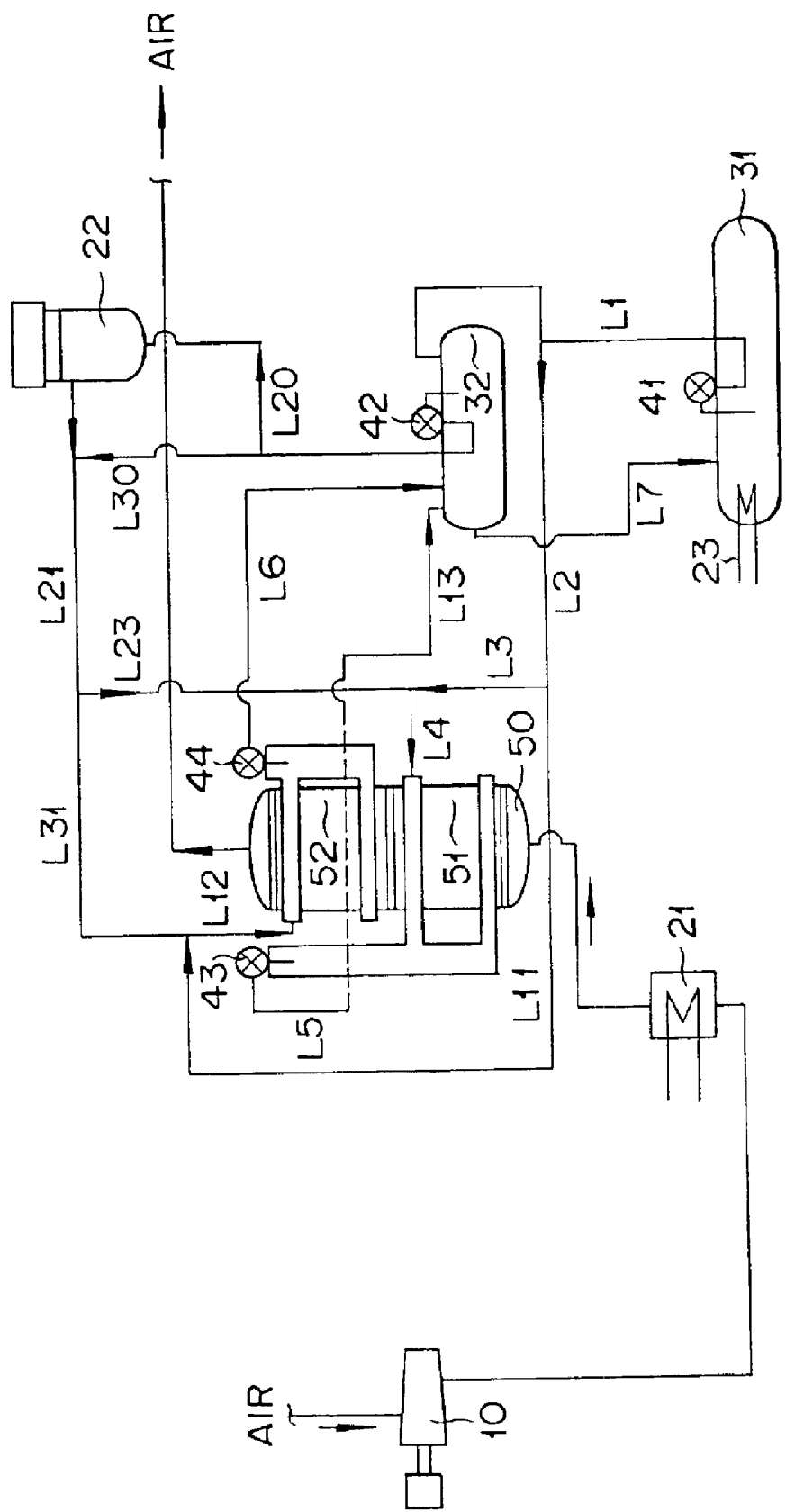
FIG. 1 is a process diagram illustrating schematically a method of this invention for starting up a reactor.
Figure 2:
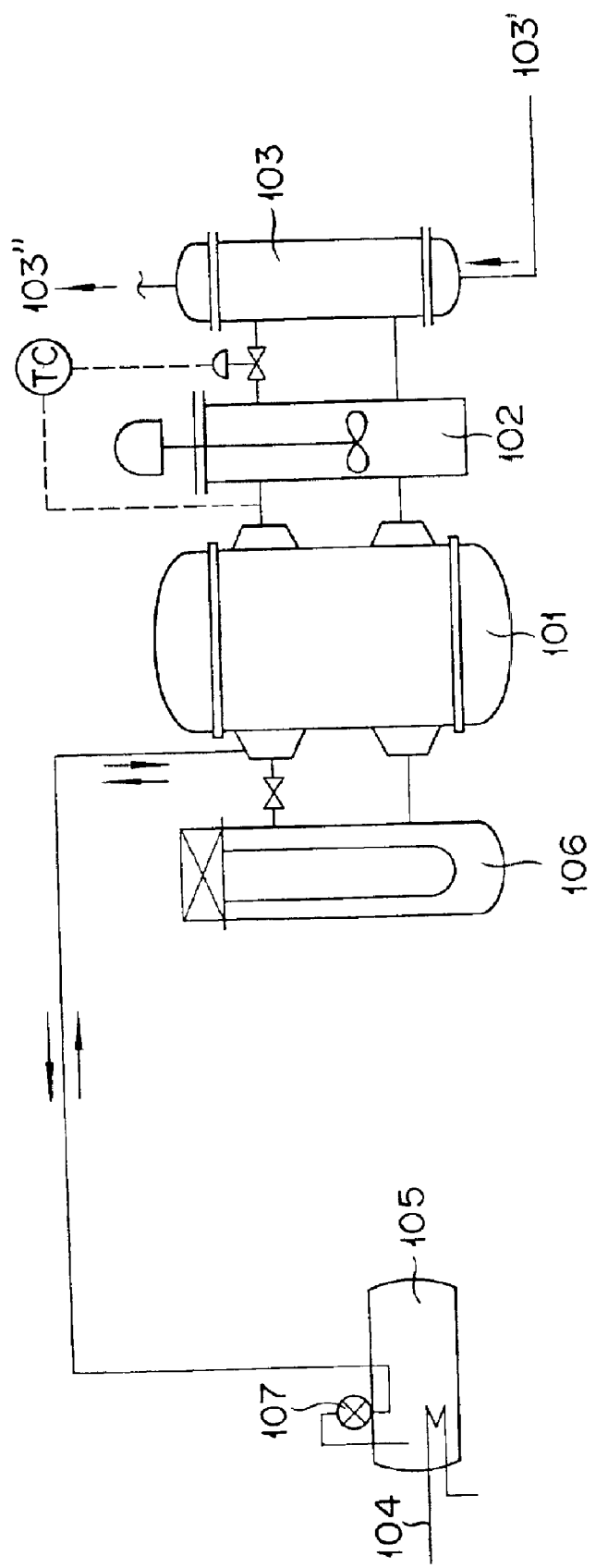
FIG. 2 is a type section illustrating a conventional reactor system and a path for the circulation of a heat medium therein.

The first aspect of this invention, in the operation of a shell-and-tube type reactor adapted to circulate to the fluid outside the tubes a heat medium having a solid point in the range of 50–250° C., relates to a method for starting up the reactor, characterized by introducing into the reaction tubesa gas heated in advance to a temperature in the range of 100–400° C. thereby starting the elevation of the temperature of the reaction tubes and subsequently circulating the heat medium heated in a heated state to the outside of the reaction tubes.

In order for the heat medium to be circulated within the reactor, it is necessary to maintain the heat medium at a temperature exceeding the solid point and enable it to retain flowability certainly. Heretofore, this flowability has been attained by heating the heat medium outside the reactor and circulating the heat medium at an elevated temperature to the reactor. When the circulation of the heat medium at an elevated temperature is a sole recourse, however, since the elevation of the temperature of the reactor requires an unduly long time, the heat medium possibly cools partly and consequently incurs solidification. This invention is aimed at providing a method for starting up the reactor which, by supplying a gas heated in advance to an elevated temperature to the reaction tubes prior to the supply of a heat medium to the reactor thereby securing the internal temperature of the reactor at a level exceeding the solid point and thereafter putting the heat medium to circulation, prevents the heat medium from being solidified again and curtails the time for elevating the temperature of the reactor. Now, this invention will be described in detail below.

The shell-and-tube type reactor to be used in this invention does not need to be particularly discriminated. Any of the reactors heretofore known to the art may be adopted. Generally, the reactor is provided on the upper and the lower side of the shell thereof each with a tube sheet, inside the shell with a plurality of reaction tubes having the opposite ends thereof retained with the tube sheets, and in the shell wall of the reactor with an inlet and an outlet for the fluid outside the tubes for the purpose of removing the heat generated inside the reaction tubes. Further, in this invention, the reactor is allowed to be furnished inside the shell thereof with built-in intermediate tube sheets adapted to partition the interior of the shell into a plurality of chambers.

The heat medium to be used as the fluid outside and encircling the tubes does not need to be particularly restricted but is only required to possess a solid point in the range of 50–250° C. The solid point is generally in the range of 50–250° C., preferably in the range of 100–200° C., and particularly preferably 130–180° C. The reason for this temperature range is that this invention contemplates starting up the reactor when the heat medium which is in a solid state at atmospheric temperature is used for circulation.

As a heat medium possessing such a solid point, niter may be cited, for example. Among other species of heat medium which are used for controlling the temperature of a chemical reaction, the niter is particularly advantageous in respect that it excels in thermal stability and exhibits the highest stability in the heat exchange performed at elevated temperatures in the range of 350–550° C.

The niter is a so-called fused salt which forms a varying composition and assumes a varying solid point. For this invention, any of the species of niter which has a solid point in the range specified above can be favorably used without reference to the type of composition. As concrete examples of the compound to be used as the niter of the description given above, sodium nitrate, sodium nitrite, and potassium nitrate may be cited. These compounds may be used either alone or in the form of a mixture of two or more members.

The gas to be introduced into the reaction tubes does not need to be particularly restricted but is only required to be incapable of exerting an adverse effect even when it is mixed with the catalyst contained in the reaction tubes and the raw material gas. Generally, the air and such inert gases as carbon dioxide, nitrogen gas, and argon gas can be advantageously used, through variable with the kind of the catalyst to be contained in the reaction tubes and the kind of the raw material gas to be supplied.

A preferred mode of embodying the method of this invention for starting up the reactor will be described with reference to FIG. 1. As illustrated in FIG. 1, 10 stands for a blower, 21, 22, and 23 each for a heater, 31 and 32 each for a tank, 41, 42, 43, and 44 each for a pump, 50 for a reactor, 51 for a first chamber, 52 for a second chamber, and L1, L2, L3, L4, L5, L6, L7, L11, L12, L13, L20, L21, L23, L30, and L31 each for a heat medium line, The tank 31 is a tank for recovering the heat medium which has been used in the reactor (heat medium recovering tank) and the tank 32 is a circulation tank for temporarily storing and circulating the heat medium. The reactor 50 is a single reactor (a reactor possessed of the first chamber 51 and the second chamber 52) and it will be described herein below on the assumption the gas heated to an elevated temperature and the heat medium are both supplied in the upflow system.

First, to the reactor 50 which encloses the reaction tubes packed with a necessary catalyst, a gas heated with the heater 21 to a temperature in the range of 100–400° C. is introduced with the blower 10. The gas is led out of the reactor 50 via an upper tube sheet of the reactor 50. In consequence of the introduction of the gas, the interior of the reactor 50 is heated to an elevated temperature from within the inside of the reaction tubes. The temperature to which the interior of the reactor is so elevated is preferred to have reached a level higher than the solid point of the heat medium to be subsequently circulated and it can be properly selected to suit the heat medium to be used. The temperature of the outlet gas of the reactor is generally in the range of 150–250° C., preferably in the range of 160–240° C., and particularly preferably in the range of 170–220° C. Since the solid point of the heat medium to be used is in the range of 50–250° C., the heat medium subsequently supplied will not incur resolidification so long as the outlet temperature of the reactor is in the range specified above. The gas and the heat medium to be supplied do not need to be fed exclusively in the upflow system but may be fed in the downflow system as occasion demands.

Subsequently, the heat medium is introduced into the first chamber 51 and the second chamber 52 of the reactor 50 and circulated therein by means of the respectively attached pumps 43 and 44 till the temperature in the chambers is elevated to a level aimed at. When the heat medium at an elevated temperature is supplied to the first chamber 51 or the second chamber 52 in the manner described above, the reactor 50 is heated by the outside of the reaction tubes owing to the elevated temperature of the heat medium and, with the aforementioned supply of the gas of an elevated temperature as a contributory factor, the rapid elevation of the temperature of the reactor is consequently accomplished.

Specifically, when the exchange of heat is performed with a heat medium which is in a solid state at atmospheric temperature, the heat medium is recovered more often than not in the recovering tank (such as, for example, the tank 31) after the use of the reactor 50. In this case, the heat medium is not suffered to remain in the reactor but is stored in the heat medium storing tank 31. The heat medium in the tank 31, therefore, is heated with the heater 23 to a degree enough to retain the fluidity thereof intact and the heat medium at an elevated temperature is then introduced into the reactor 50.

The introduction of the heat medium into the reactor 50 is attained by introducing the heat medium in the tank with the pump 41 to the tank 32 via the line L1 and then supplying it from the tank 32 with the pump 42 to the first chamber via the lines L20 (or L30), L21, L23, and L4 and to the second chamber via the lines L20 (or L30), L21, L31, and L12.

Incidentally, the heat medium in the tank 31 may be directly introduced into the reactor 50 without passing the tank 32 at the time of starting up the reaction. The introduction of the heat medium into the first chamber 51 is attained via the lines L1, L2, L3, and L4. The introduction of the heat medium into the second chamber 52 is effected via the lines L1, L2, L11, and L12. The tank 32 is installed for the purpose of circulating the heat medium and, therefore, is furnished with a smaller volume than the heat medium storing tank 31 which serves the purpose of recovering the heat medium after the use thereof in the reactor. When the heat medium in the tank 31 is introduced into the tank 32 and then introduced further into the component chambers, it becomes necessary to continue the operation of introducing the heat medium from the tank 31 and subsequently delivering it to the component chambers while keeping the liquid level in the tank 32 under observation, with the result that the management of the liquid level in the tank 32 will be complicated. When the heat medium is introduced for the first time into the component chambers at the time of starting up the reactor, therefore, it is convenient to introduce the heat medium from the tank 31 directly into the component chambers without being passed through the tank 32.

Then, the heat medium introduced into the reactor is fated to be circulated inside the component chambers with the respectively attached pump 43 and 44. At times, however, the temperature in the reactor will not be elevated to a target level by simply introducing and circulating the heat medium which has been heated at first. The reason for this failure is that the reactor itself removes the heat medium of its heat and generally induces the temperature of the heat medium to decline. In this case, the failure is precluded by causing the heat medium being circulated inside the chamber to be extracted from the chamber, heated to a necessary level, and then introduced again into the chamber.

To be specific, the preclusion is implemented, for example, by connecting each of the chambers to the tank 32 thereby permitting at least part of the heat medium in the chambers to be introduced into the tank 32, heating the introduced part of the heat medium with the heater 22, and then circulating the heated part of the heat medium to the chamber. The circulation of the heat medium in the first chamber to the tank 32, for example, is attained via the lines L5 and L13. Then, the circulation of the heat medium in the second chamber is attained via the line L6. By advancing the heat medium in the tank 31 with the pump 42 to the heater 22 via the line L20 and heating it with the heater 22, it is made possible to elevate the temperature of the reactor 50 by the circulation of the heat medium in the heated state to at least one of the chambers via the lines L21, L23, and L4 or via the lines L21, L31, and L12. Incidentally, by introducing the heat medium in the tank 32 via the lines L30 and L21 to the chamber without being passed through the heater 22, it is made possible to introduce the heat medium not in the heated state into the chamber. The path for the heat medium may be selected by any of the methods known to the art. The heat medium circulated in the chamber does not need to be circulated wholly via the tank 32. The heat medium in the second chamber 52, for example, may be circulated exclusively in the chamber.

When the liquid level in the tank 32 rises, the liquid overflows this tank 32 and finally reaches the tank 31 via the line L7. When the heat medium flows in through each of the chambers or the temperature in the tank rises, for example, the line L7 is used on the condition that the amount of the heat medium forwarded from the tank 31 is large.

This invention can be applied to the case of retaining the heat medium in the reactor and solidifying it therein. Specifically, when the gas at an elevated temperature is introduced into the reactor as described above, the heat medium remaining inside the reactor is caused by the temperature of the gas introduced into the reaction tubes to assume fluidity eventually. When the heat medium heated with the heater 22 installed outside the reactor is further circulated, therefore, the temperature of the reactor 50 can be elevated by the heat of the heat medium. The temperature of the heat medium to be circulated to the reactor 50 does not need to be particularly restricted but may be properly selected for the purpose of enabling the reactor to assume a temperature optimum for the catalytic reaction aimed at. Though the gas and the heat medium may be supplied to the reactor not only in the upflow system but also in the downflow system, the gas is preferably supplied in the downflow system on account of greater effectiveness. Since the heat medium in a solidified state is melted from the upper part thereof downward and the gravitation is consequently added to the flow of the heat medium, the heat medium is quickly melted and heated to an elevated temperature.

When the reactor is enabled to secure a necessary temperature in consequence of the circulation of the heat medium as described above, the operation of starting up is terminated by stopping the heater 22. When the heat medium is circulated to the reactor 50 after it has been heated with the heater 22, the supply of the gas of the elevated temperature into the reactor may be stopped because the heat medium has no great possibility of succumbing to resolidification.

Now, the relation between the temperature of the gas in a heated state and the temperature of the heat medium circulated to the reactor 50 will be described below. When the gas of the elevated temperature introduced into the reactor 50 is lower than the temperature of the heat medium, for example, the supply of this gas is preferred to be stopped because it interferes with the elevation of the temperature of the reactor 50. In contrast, when the temperature of the gas is higher, the introduction of the gas at the elevated temperature may be safely continued during the circulation of the heat medium. Since the reactor 50 does not need to be elevated beyond the temperature fit for the purpose of use and since the undue elevation of temperature rather obstructs the reaction, it is proper to select the optimum temperature.

When acrylic acid is produced in a single reactor, for example, the gas at an optimum temperature must be supplied severally to the first chamber and the second chamber because the reaction temperature in the second chamber is lower than that in the first chamber in an ordinary use of the reactor. In this case, the single reactor can be started up with excellent thermal efficiency by introducing the heat medium of a temperature conforming to the temperature of the chamber on the lower temperature side to each of the chambers and circulating the heat medium in a heated state exclusively to the chamber on the higher temperature side. When the heat medium heated to a still higher temperature is circulated exclusively to the first chamber 51 which is on the higher temperature side, the heat medium led out of the tank 32 is heated with the heater 22 and then circulated only to the first chamber 51. In this case, the heat medium to be circulated to the second chamber 52 may be circulated exclusively within the second chamber 52 without being circulated to the tank 32. Even in this case, the temperature of the heat medium in the second chamber is elevated by the gas heated to an elevated temperature by the heat medium circulated in the adjoining chamber and/or the first chamber. The supply of the gas, therefore, is stopped depending on the temperature conditions of the first chamber and the second chamber.

In this invention, when the heat medium circulated in the chamber is further heated and then put to circulation again, the chamber on the higher temperature side may be the first chamber 51 or the second chamber 52. Preferably, however, the chamber on the higher temperature side adjoins the inlet for the gas mentioned above. The reason for this preference is that the gas is more often than not required to have a higher reaction temperature in the first chamber. After the reactor has reached the optimum temperature in the manner described above, the operation of starting up the reactor is terminated by stopping the operation of the heater 22.

After the operation of starting up the reactor is terminated, the product aimed at can be manufactured by supplying the raw material gas to the interior of the reactor.

The method of this invention for starting up the reactor can be particularly favorably used in starting up a reactor which is used for producing acrylic acid, methacrylic acid, acrolein, or methacrolein, for example. The acrylic acid and so on mentioned above are compounds to be produced and consumed in large quantities. The reactors to be used for their production, therefore, are proportionately large. It is difficult to heat such reactors to elevated temperatures. The present invention is particularly suitable for heating such large reactors to elevated temperatures at the time of starting up these reactors.

Now, the method for starting up a shell-and-tube type reactor which is used for the production of acrylic acid will be described specifically with reference to FIG. 1.

Acrylic acid is produced by supplying a raw material gas such as propylene, propane, or acrolein to a known reactor incorporating therein reaction tubes packed with an oxidizing catalyst and thereby inducing a reaction of catalytic gas phase oxidation of the raw material gas in the reaction tubes. Generally, the reaction of catalytic gas phase oxidation of a raw material gas is initiated by supplying a molecular oxygen-containing gas and an inert gas in respectively prescribed amounts to the raw material gas. Consequently, acrolein is formed by using propylene as the raw material gas. Then, acrylic acid is obtained by subjecting acrolein similarly to a reaction of catalytic gas phase oxidation.

In the reaction of catalytic gas phase oxidation, since the reaction tubes are heated by the heat of reaction to a temperature in the range of 250–450° C., the niter having a solid point in the range of 130–180° C. is generally used as the heat medium, i.e. a fluid circulated outside the reaction tubes. The method of this invention for starting up the reactor is preferred to use as the gas for introduction into the reaction tubes an inert gas incorporated in the raw material gas during the manufacture of a target product, a molecular oxygen-containing gas such as, for example, air. When the reactor 50 is partitioned with an intermediate tube sheet into a first chamber 51 and a second chamber 52 as illustrated in FIG. 1, reaction tubes through these chambers are respectively packed with catalysts which fit the reactions induced in the chambers and different gas components can be moved in the interiors of the reaction tubes through the first chamber and the second chamber. The gas of an elevated temperature to be used, therefore, is required to be stable even on exposure to any of the catalysts and the component gases. The reason for this stability is that even when the raw material gas is supplied to the reactor which has been heated to an elevated temperature, the elevated temperature brings no effect on the raw material gas or the reaction catalyst.

The temperature of the gas under discussion is preferred to have been set at a level higher than the solid point of the niter by the time that the gas is supplied to the interiors of the reaction tubes. This elevation of the temperature of the gas may be attained by burning a fuel in a furnace or by using an electric heater. When the volume of the heat to be supplied is large, it is advantageous from the viewpoint of the thermal economy to effect the temperature elevation of the gas by the use of steam. Then the outlet temperature of the reactor is set at a level in the range of 100–400° C. and preferably at a level equal to or higher than the solid point of the niter in use. Even when the heat medium is put to circulation thereafter, this elevation of temperature will be at an advantage in preventing the heat medium from being resolidified, enabling the elevation of temperature to proceed quickly, and decreasing the effect of the product of solidification on the devices in use. This invention aims the supply of the gas to the reaction tubes at the primary object of smoothing the circulation of the heat medium.

Incidentally, in the production of acrylic acid by the two-stage catalytic gas phase oxidation of a propylene-containing gas, the known oxidizing catalyst generally used in the production of acrolein by the reaction of catalytic gas phase oxidation of a raw material containing propylene can be used as the former-stage catalyst. The latter-stage catalyst does not need to be particularly discriminated. The oxidizing catalyst which is generally used in the production of acrylic acid by the gas phase oxidation of a reaction gas mainly containing the acrolein obtained in the former stage by the two-stage method for catalytic gas phase oxidation can be used as the latter-stage catalyst. The shape of the catalyst is not particularly restricted. The catalyst may be in the shape of spheres, columns, cylinders, etc.

Subsequently, the temperature elevation of the interior of the reactor is attained by supplying the heat medium of an elevated temperature to the preheated reactor, with the result that the reactor will be heated to the elevated temperature from the inside and the outside of the reaction tubes.

Since the heat medium is in a solid state at atmospheric temperature, the heat medium which has been used in the reactor 50 is more often than not led out of the reactor and stored in the tank (heat medium recovering tank) 31 for the recovery of the heat medium. The heat medium in the tank 31, therefore, is heated with the heater 23 till it assumes a fluid state and the heat medium in the fluid state is subsequently introduced into the reactor by dint of the pressure of the attached pump 41. The heat medium may be introduced via the tank 32 as described above or may be directly introduced from the tank 31 into the component chambers.

The heat medium which has been introduced into the component chambers is circulated with the respectively attached pumps 43 and 44. These pumps are preferred to be axial pumps because the reactor is large in size and the heat medium is also large in volume and the heat medium in such a large volume must be circulated without inducing an undue load. The temperature of the heat medium to be used is only required to exceed the solid point of the heat medium and enable the catalyst packed in the reaction tubes to secure the optimum temperature.

Then, the reactor 50 to which the heat medium is introduced has the component chambers thereof connected to the tank 32 so that at least part of the heat medium in the component chambers may be introduced into the tank 32. Since the reactor for acrylic acid, for example, is large in size, the volume of the catalyst varied by the elevation of the temperature of the heat medium is proportionately large. This change of the volume, therefore, can be easily relaxed by leading out into the tank 32 the portion of the heat medium which has overflowed the reactor in consequence of the variation mentioned above.

When a single reactor is used where the acrylic acid is obtained by a two-stage reaction, the first stage for producing acrolein from propylene as a raw material gas and the second stage for producing acrylic acid by further oxidizing the acrolein, the catalysts used in the component chambers are different and the inner temperatures of the chambers optimum for the reaction are also different. In this case, the temperature of the interior of the reactor can be elevated conveniently and economically by supplying the heat medium of an elevated temperature exclusively to either of the chambers. Particularly, in the reaction of catalytic gas phase oxidation of acrylic acid, the chamber on the downstream side of the raw material gas may be at a lower temperature. When the heat medium at a still higher temperature is circulated on the upstream side, the catalyst in the chamber on the downstream side is also heated to an elevated temperature by the exposure to the higher temperature. In consideration of the thermal economy, therefore, the heat medium heated in advance is circulated exclusively to the first chamber. From the viewpoint of the characteristic behavior of the reaction temperature described above, the reactor for the production of acrylic acid or methacrylic acid is preferred to be started up by circulating the heat medium of an elevated temperature to the chamber which adjoins the inlet for the gas of an elevated temperature.

The circulation of the heat medium at different temperatures to the component chambers in the operation of starting up the reactor for acrylic acid, for example, is accomplished by introducing the heat medium fated to be circulated to the first chamber 51 exclusively into the tank 32, then heating the heat medium therein with the heater 22, and circulating the heat medium of an elevated temperature exclusively to the first chamber 51. In this case, the heat medium in the second chamber 52 is circulated exclusively within the second chamber. The increment of the heat medium which has been produced by the temperature elevation is recovered in the tank 32 to which the second chamber 52 is connected.

When the interior of the reactor has been heated to a target temperature owing to the circulation of the heat medium, the operation of starting up the reactor is terminated by stopping the operation of the heater.

By starting up the reactor and then supplying the raw material gas to the reactor and producing acrylic acid by a known method, the product aimed at can be manufactured quickly in the reactor which has been heated to an elevated temperature. The production of methacrylic acid can be similarly implemented by changing the raw material gas.

The second aspect of this invention resides in a reactor system comprising a reactor forming therein a plurality of chambers partitioned with an intermediate tube sheet, means for storing a heat medium led out of the chambers, heating means for heating the heat medium led out of the storing means, and means for supplying the heat medium heated with the heating means to an elevated temperature to at least one of the chambers, characterized by the fact that the storing mean comprises one tank capable of storing at least part of the heat medium in the chambers and the tank has a volume smaller than the amount of the heat medium circulated within the component chambers.

This invention concerns a reactor system which particularly suits the purpose of introducing portions of a heat medium having different temperatures into a plurality of chambers thereby imparting proportionately different inner temperatures to the chambers and leading out portions of the heat medium differing in temperature from the chambers. This system does not need to be limited to the case of circulating the heat medium for the purpose of elevating the temperature of the reactor at the time of normal operation thereof and the case of elevating the temperature of the reactor at the time of starting up the reactor but is only required to be capable of elevating the inner temperatures of the chambers to different levels by circulating portions of the heat medium differing in temperature. The temperature elevation of this nature is required by the reactor which is intended to effect an endothermal reaction.

The reactor system mentioned above is characterized by displaying in the operation of preheating a heat medium thereby enabling it to secure fluidity and further heating and circulating the heat medium in a fluid state to the reactor, the ability to circulate the heat medium in a heated state to a plurality of chambers by the use of one heating means and relax the increase brought about by the heating in the volume of the heat medium by the use of one tank.

Now, the characteristic of the reactor system of this invention will be described below with reference to FIG. 1.

First, the change in volume caused by the temperature elevation of the heat medium can be recovered as follows.

First, when the heat medium is heated, it has the volume thereof increased as described above. When such a large tank (tank 31 illustrated in FIG. 1) as is used for recovering the heat medium after the termination of the operation of the reactor is used for the purpose of recovering this change of volume, the pump 41 attached to the tank 31 is eventually actuated to lead the heat medium out of the tank and the liquid level in the tank is lowered in consequence of only a slight change in the volume of the heat medium as compared with the volume of the tank. The pump 41 is allowed to operate under the condition that no cavitation be induced by the operation. When the heat medium is circulated in only a small volume as compared with the volume of the tank, the pump is fated to incur a load because it tends to induce cavitation. Thus, the pump is connected to the tank 32 having a smaller volume than the tank 31 and this tank 32 is utilized for recovering the change of the volume. Since the tank 31 is intended to recover and store the whole volume of the heat medium in the reactor, it has a larger volume than the total volume of the portions of heat medium in the chambers. The one tank which as means for storing the heat medium of this invention is capable of storing at least part of the portions of the heat medium in the component chambers is required to have a volume smaller than the volume of the heat medium circulated within the chambers. Properly, this volume is in the range of 5–80 vol. %, preferably in the range of 10–50 vol. %, of the amount of the heat medium circulated within the component chambers.

The amount of the heat medium circulated within the chambers according to this invention is defined by the formula:

$$(\pi/4)(D^2-d^2\times n)\times(L-t)\times N$$

wherein N stands for the number of reactors, D for the inside diameter of a reactor, t for the total thickness (upper tube sheet+intermediate tube sheet+lower tube sheet) of the tube sheets of the reactors, d for the outside diameter of the reaction tube, L for the length of the reaction tube, and n for the number of reaction tubes.

In this invention, it suffices to have only one tank connected to the plurality of chambers. If tanks are disposed one for each of the chambers for the purpose of recovering the change in temperature of the heat medium, the equipment will be complicated and the cost of design will be exalted. By connecting the chambers to one tank thereby enabling the portions of the heat medium in the chambers to be introduced into the one tank, it is enabled to simplify the layout of pipes and decrease the number of pipes, consequently enhance the thermal efficiency, and relax the load imposed on the pumps attached to the large tank.

Further, by introducing the heat medium in the component chambers into the one tank (tank 31) as described above, it is made possible to decrease the number of heaters to one because the heat medium in the tank can be heated with the heater and then the heat medium of an elevated temperature can be supplied to the component chambers. Moreover, the supply of portions of heat medium differing in temperature to the component chambers can be realized by distributing pipes for circulation of heat medium between the tank 32 and the heater 22 and between the tank 32 and the component chambers 51 and 52.

The reactor to be used in the reactor system is preferred to be provided with heating means to be used for the gas introduced into the reaction tubes. By virtue of this heating means, the first aspect of this invention can be easily embodied.

The reactor system of this invention can be used for producing (meth)acrylic acid and (meth)acrolein because the reactor is possessed of the first chamber and the second chamber. More often than not these compounds use the reactor with the component chambers thereof set at different temperatures as described above. When the reactor system of this invention is used, the component chambers of the reactor can be easily heated to their respectively optimum elevated temperatures.

In the reactor system of this invention, the pipe for introducing the heat medium into the reactor is preferred to be connected to the reactor from the upper annular conduit of the reactor or from the part at a level higher than the annular conduit. The expression "the upper annular conduit of the reactor or the part at a level higher than the circular conduit" as used in this invention embraces, in addition to the upper annular conduit (the parts indicated by 63 and 64 in FIG. 1, for example), the lower end of the upper annular conduit, the shell of the reactor located at a level higher than the lower end, the axial pump for supplying the heat medium into the shell of the reactor, and the pipe for introducing the heat medium from the axial pump to the shell of the reactor.

When the heat medium is introduced via the upper annular conduit of the reactor, the heat medium flows down the interior of the reactor. In contrast, when the heat medium is introduced from the attached axial pump, the heat medium flows down the interior of the axial pump and then flows up the interior of the reactor from the lower part of the axial pump. Generally, even after the reactor is filled to capacity with the heat medium, the heat medium is supplied continuously and allowed to overflow the reactor. The heat medium to be supplied to the interior of the reactor has the possibility of being deprived of the heat by not only the pipes laid to reach the reactor but also the reactor and the axial pump themselves and consequently solidified within the axial pump and the reactor. When the heat medium introduced via the pipes is supplied downflow during the introduction into the axial pump and the reactor, the load imposed on the pump (the pump 32 in FIG. 1, for example) serving the purpose of circulating the heat medium can be relaxed because the heat medium falls by dint of the gravitation. If the heat medium is supplied upflow, the pressure will be increased and the load on the pump circulating the heat medium will also increase because solid matter tends to induce clogging.

After the reactor is filled to capacity with the heat medium, the axial pump (the pumps 43 and 44 in FIG. 1, for example) is actuated. When the axial pump is designed from the beginning to advance the heat medium upflow or downflow inside the reactor, the direction of flow of the heat medium can be secured as initially designed after the reactor has been filled to capacity with the heat medium.

The third aspect of this invention resides in a reactor system comprising a reactor, means for storing a heat medium led out of the chambers, heating means for heating the heat medium led out of the storing means, and means for supplying the heat medium heated by the heating means to an elevated temperature to at least one of the chambers, characterized by the fact that the storing mean comprises one tank capable of storing at least part of the heat medium in the component chambers, that the volume of the tank is smaller than the amount of the heat medium circulated within the component chambers, and that the pipe for introducing the heat medium into the reactor is connected to the reactor from an upper annular conduit of the reactor or from the part at a level higher than the annular conduit.

The heat medium varies the volume thereof in accordance as the temperature thereof is varied. The necessity for relaxing this variation of the volume is not limited to a single reactor. By using one tank capable of storing at least part of the heat medium in the component chambers as the storing means mentioned above and designing this tank with a volume smaller than the amount of the heat medium circulated within the component chambers, therefore, it is made possible to effect easy storage of the increase in the amount of the heat medium. Moreover, by connecting the pipe for introducing the heat medium to the reactor to the reactor from the upper annular conduit of the reactor or from the part at a level higher than the annular conduit, it is made possible to relax the load imposed on the pump in consequence of the solidification of the heat medium in the same manner as described above. For the purpose of advancing the heat medium upflow inside the reactor after the reactor has been filled to capacity with the heat medium, it suffices to design the axial pump (the pump 43 or 44 in FIG. 1, for example) to advance the heat medium upflow from the beginning.

EXAMPLE

Now, this invention will be described more specifically below with reference to a working example.

Example I

In an apparatus constructed as illustrated in FIG. 1, a shell-and-tube type reactor was started up by using a niter composed of 50 weight % of potassium nitrate and 50 weight % of sodium nitrite as a heat medium and air as a gas of an elevated temperature to be introduced into the reactor. The niter was stored in the tank 31 and not allowed to remain in the reactor before the reactor was started up.

The shell-and-tube type reactor used herein had an inside diameter of 4000 mm and was provided in the upper part and the lower part of the shell thereof respectively with tube sheets, which supported 9300 reaction tubes of a length of 6500 mm as nipped therebetween. At a position 3200 mm upward from the lower tube sheet, an intermediate tube sheet was disposed so as to partition the interior of the reactor into two chambers. Further, the upper chamber 52 and the lower chamber 51 of the reactor are provided respectively with annular conduits. The axial pumps 43 and 44 are attached respectively to the annular conduits.

First, air was preheated to a temperature of 210° C. in the preheater 21 with steam of a gauge pressure of 4 Mpa. By supplying the preheated air with the blower 10 in a flow volume of 190 Nm$^3$/min to the reactor 50, the gas temperature at the outlet of the reactor (the outlet of the second chamber) was elevated to 200° C. (the first step).

After the rise of the outlet temperature of the reaction gas till 200° C. was confirmed, the heat medium preheated with the attached heater 23 to 200° C. was introduced with the pump 41 from the tank 31 to the reactor 50. The heat medium was introduced to the first chamber 51 from the tank 31 via the lines L1, L2, L3, and L4 and to the second chamber 52 from the tank 31 via the lines L1, L2, L11, and L12. Then, after the heat medium had been introduced into the reactor 50, the axial pumps 43 and 44 attached respectively to the component chambers were actuated to put the portions of heat medium in the component chambers to circulation within the component chambers. The component chambers were connected to the tank 32 so that part of the heat medium in the component chambers was circulated from the first chamber to the tank 32 via the lines L5 and L13 and from the second chamber 52 to the tank 32 via the line L1 (second step).

Then, the blower 10 was stopped and, at the same time, the pump 42 attached to the tank 32 was actuated to circulate the heat medium in the tank 32 to the electric heater 22 of a capacity of 700 kW and elevate the temperature of the heat medium therein. The heat medium thus heated to the elevated temperature was supplied exclusively to the first chamber 51 via the lines L21, L23, and L4. Consequently, the second chamber 52 was preheated by the first chamber 51 to the elevated temperature (third step).

Since the temperature of the heat medium in the first chamber 51 reached 350° C. and the temperature of the heat medium in the second chamber 52 reached 260° C., i.e. the prescribed temperatures for the reaction, the heater 22 was stopped to terminate the operation of starting up the reactor. The time required for this operation was 36 hours.

Figure 3:
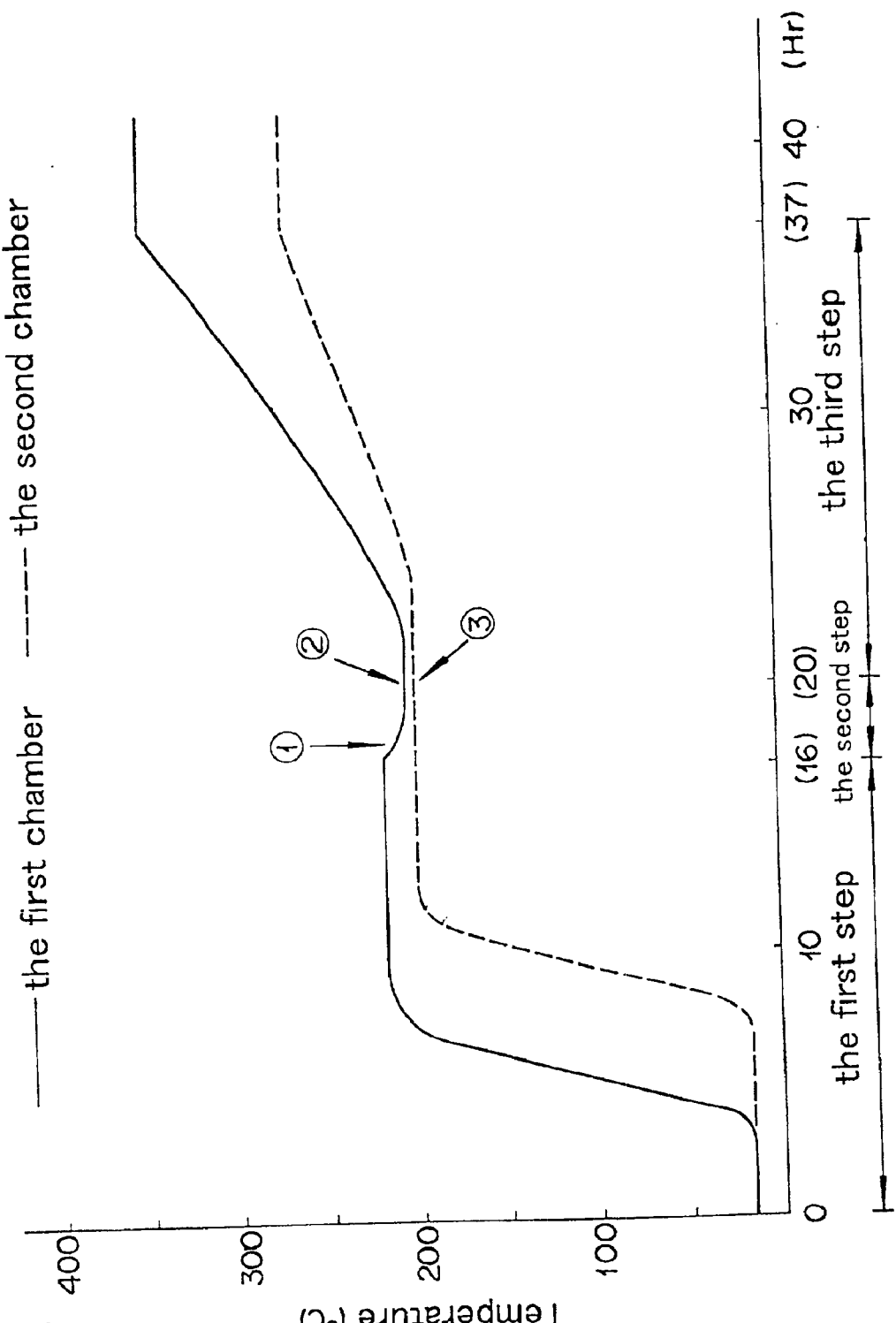
FIG. 3 is a diagram showing changes of temperature observed in the component chambers of the reactor when the method for starting up the reactor was performed as described in Example 1.

The changes in temperature of the component chambers which were observed when the reactor was performed by the method of the working example are shown in FIG. 3. In the diagram of FIG. 3, ① denotes the time for starting the operations of the pumps 43 and 44, ② the time for starting the operations of the pump 42 and the heater 22, and ③ the time for stopping the blower.

Comparative Example

In the same apparatus as used in the working example, the reactor was started up by following the procedure thereof while omitting the supply of the gas at an elevated temperature to the reactor 50 prior to the supply of the heat medium.

Specifically, the heat medium heated with the attached heater 23 to a temperature of 200° C. was introduced with the pump 41 to the first chamber 51 from the tank 31 via the lines L1, L2, L3, and L4 and to the second chamber 52 from the tank 31 via the lines L1, L2, L11, and L12.

Then, after the heat medium had been introduced into the reactor 50, the axial pumps 43 and 44 attached respectively to the component chambers were actuated to put the portions of heat medium in the component chambers to circulation within the component chambers. In the same manner as in the working example, the component chambers are connected to the tank 32 so that the heat medium was circulated from the first chamber 51 to the tank 32 via the lines L5 and L13 and to the second chamber 52 from the tank 32 via the line L6.

Since the temperature of the heat medium in the reactor consequently fell to 158° C., the pump 42 was actuated to circulate the heat medium to the electric heater 22 of a capacity of 700 kW and heat the heat medium to an elevated temperature. The heat medium which had been heated to the elevated temperature was supplied, similarly in the working example, exclusively to the first chamber 51. Incidentally, the second chamber 52 was preheated to an elevated temperature with the heat of the first chamber 51. Since the temperature of the heat medium in the second chamber 52 reached 350° C. and the temperature of the heat medium in the first chamber 51 reached 260° C., i.e. the prescribed temperatures for the reaction, the operation of starting up the reactor was terminated. The time required for this operation was 62 hours.

What is claimed is:

1. In a shell-and-tube type reactor adapted to circulate a heat medium having a solid point in the range of 50–250° C. to the outside of the reaction tubes, a method for starting up the reactor characterized by introducing a gas of a temperature in the range of 100–400° C. into the reaction tubes thereby initiating temperature elevation and then circulating the heat medium in a heated state to the outside of the reaction tubes wherein said heat medium is a niter.

2. A method according to claim 1, wherein said circulation of the heat medium is started after the temperature of said gas at the outlet of said reactor has reached a level in the range of 150–250° C.

3. A method according to claim 1, wherein said shell-and-tube reactor forms therein a plurality of chambers partitioned with an intermediate tube sheet.

4. A method according to claim 3, wherein said temperature elevation of the reaction chamber is initiated by introducing the gas at a temperature in the range of 100–400° C. into the reaction tubes through chambers and then said temperature elevation is continued by circulating the heat medium in all the component chambers to the outside of the reaction tubes.

5. A method according to claim 3, wherein said temperature elevation of the reaction chamber is initiated by introducing the gas at a temperature in the range of 100–400° C. into the reaction tubes through chambers and then said temperature elevation is continued by circulating the heat medium in all the component chambers to the outside of the reaction tubes and circulating the heat medium further heated in at least one of the chambers to the outside of the reaction tubes.

6. A method according to claim 5, wherein the chamber in which the heat medium in the heated state is circulated adjoins the inlet for said gas.

7. A method for the production of (meth)acrylic acid and/or (meth)acrolein, characterized by supplying a raw material gas to said reactor after the method for starting up the device set forth in any of claim 1.

8. A method according to claim 1, wherein said niter comprises a fused salts mixture.

9. A method according to claim 1, wherein said niter comprises one or more salts selected from the group consisting of sodium nitrites, sodium nitrate, potassium nitrate and mixture thereof.

* * * * *